United States Patent [19]

Szemler et al.

[11] Patent Number: 4,659,661
[45] Date of Patent: Apr. 21, 1987

[54] PROCESS FOR THE PREPARATION OF FERMENTATION BROTH FOR COENZYME $B_{12}$ AND OTHER CORRINOID PRODUCTION

[75] Inventors: László Szemler; Eva C. Pechány; Mária Langer; Gyula Hruby, all of Budapest; Valéria Sike, Almásfüzitó, all of Hungary

[73] Assignee: Richter Gedeon Vegyeszeti Gyar R.T., Budapest, Hungary

[21] Appl. No.: 648,792

[22] Filed: Sep. 7, 1984

[30] Foreign Application Priority Data

Sep. 16, 1983 [HU] Hungary ............................. 3210/83

[51] Int. Cl.$^4$ ...................... C12P 19/42; C12P 39/00; C12N 1/20; C12R 1/01
[52] U.S. Cl. ...................................... 435/86; 435/253; 435/42; 435/822
[58] Field of Search .................... 435/86, 253, 42, 822

[56] References Cited

U.S. PATENT DOCUMENTS 3,979,259  9/1976  Johan et al. ............................ 435/86

OTHER PUBLICATIONS

Szemler et al. "Separation of Fermentation Broths Following Vitamin $B_{12}$ Fermentation with Methanobacterium" Chem. Abstracts, vol. 99 -7f 193171g (1983).
Guyton 1976 *Textbook of Medical Physiology* W. B. Saunders Phil. p. 103.

*Primary Examiner*—Thomas G. Wiseman
*Assistant Examiner*—Joanne M. Giesser
*Attorney, Agent, or Firm*—Karl F. Ross; Herbert Dubno

[57] ABSTRACT

The invention relates to a process for the preparation of a fermentation broth containing coenzyme $B_{12}$, with a new, anaerobic, mesophilic, methane-producing mixed micropopulation, under anaerobic, septic conditions, using a new broth containing methanol, precursors and partially known nutrients, In the new process according to the invention the improvement consists in (a) removing 5 to 15 volume percent of the inoculum fermentation broth containing the anaerobic, mesophilic, methan-producing new mixed micropopulation and replacing same with an equal volume of a broth containing cornsteep liquor hydrolysate and/or corn slops of hydrolysate thereof and other known nutrients, the number and concentration of which has been reduced, for 6 to 8 days, and if desired, further manufacturing the fermentation broth removed, (b) after reaching an assimilation velocity of at least 0.15 to 0.2 g methanol/lit. fermentation broth/hour, continuing removal of the fermentation broth as described in step (a) but replacing same with a broth supplemented with ammonium sulfate and o-xylidine, and continuing fermentation for 6 to 8 days, and if desired, further manufacturing the fermentation broth removed, (c) after achieving an assimilation velocity of 0.2 to 0.3 g methanol/lit. fermentation broth/hour—i.e. after converting the inoculum fermentation broth into a maintaining fermentation broth—continuing removal of the fermentation broth and addition of fresh broth as described in step (b), and if desired, interrupting the removal of fermentation broth for several days, and (d) adding of the removed maintaining fermentation broth on the first day nutrients according to step (b), and if desired, on the second day only methanol, cornsteep liquor or cornsteep liquor hydrolysate and ammonium carbonate and further manufacturing the fermentation broth obtained, which is suitable for batchwise production, and (e) repeating steps (a), (c) and (d) daily.

6 Claims, No Drawings

PROCESS FOR THE PREPARATION OF FERMENTATION BROTH FOR COENZYME $B_{12}$ AND OTHER CORRINOID PRODUCTION

The invention relates to a process for the preparation of a fermentation broth producing coenzyme $B_{12}$ and other corrinoids (e.g. factor III) by using a new, mesophilic, methane-producing mixed micropopulation under anaerobic, septic conditions, and a new broth containing known precursor(s) and partially known nutrients.

Though in the process according to the invention the precursor(s) and certain components of the broth are known, the number and proportion of nutrients and the quantity of nutrients required for coenzyme $B_{12}$ production are essentially lower than in the conventionally used processes, accordingly, the broth used in the process according to the invention is new.

The fermentation broth according to the invention after drying or heat treatment, can be used for the preparation of animal fodder or fodder additives (premixes), or if desired, for vitamin $B_{12}$ (cyanocobalamine) production for use either in human or in veterinary therapy.

It is known that in the microorganism cells used for vitamin $B_{12}$ fermentation instead of vitamin $B_{12}$ other corrinoids (coenzyme $B_{12}$) are accumulated, in which to the central cobalt atom of the corrinoid skeleton a desoxyadenosyl group is attached instead of a cyanide group.

Throughout this specification and claims under active ingredient is the mixture of active corrinoids coenzyme $B_{12}$ and factor III are meant [Biol. Chem. 235, 480 (1960)].

According to the literature inoculum is a "virus solution, microorganism or cell suspension or vegetable organ, tissue or cell used for the production of new, sterile cultures" (Straub, F. B.: Biological Enzyclopedia II. p. 287, Akadémiai Kiadó, Budapest (1978)). The inoculum according to the invention contains an anaerobic, septic, mesophilic, methane-producing mixed micropopulation.

Precursor as used hereinafter is a starting compound from which the desired end product is prepared by a series of biological reactions (ibid. III, 437, e.g. 5,6-dimethylbenzimidazole, cobalt chloride, etc.).

The broth is a culture medium prepared for use in the fermentation growth of microorganisms. The broth contains all nutrients needed by the microorganisms during fermentation in an assimilable form (ibid. IV. 249; e.g. methanol, ammonium bicarbonate, magnesium chloride, etc.). Under the term "broth" as used hereinafter we mean a culture medium containing a combination of nutrients and precursors.

Nutrients are chemical substances which are vital for the micropopulation, e.g. carbon and nitrogen sources. In the process according to the invention methanol plays a double role: it is a carbon source in the biosynthesis, and at the same time provides the energy required for the formation of mixed micropopulation.

Semicontinuous fermentation means that the formation of mesophilic, methane-producing, mixed micropopulation is continuous while the removal of fermentation broth and the addition of nutrients are carried out periodically, preferably once or twice a day.

The aim of the semicontinuous "maintaining" fermentation used in the process according to the invention is to preserve (maintain) the composition of the new, mesophilic, methane-producing mixed micropopulation according to the invention for a longer period, at a relatively low active ingredient content. By this fermentation step a starting fermentation broth is provided for the batchwise, "producing" fermentation (here the active ingredient concentration is high), periodically, preferably one or two times a day.

For the production of coenzyme $B_{12}$ there are numerous fermentation processes and technologies known in the art. The majority of the fermentation are aerobic, sterile procedure. The advantage of these processes is that they produce specifically more coenzyme $B_{12}$, but under such conditions the production costs are high, more complicated equipment is required, and there is a danger of infection.

By contrast with the aerobic, aseptic fermentation, the anaerobic, septic fermentation, though provides a lower specific coenzyme $B_{12}$ production, is considerably simpler and cheaper. The biogas formed as a by-product during fermentation is a valuable energy source having a high heat value.

Biosynthesis of coenzyme $B_{12}$ is summarized by J. Florent and L. Ninet (E. J. Peppler and D. Perlman: Microbial Technology, 2nd Ed., Vol. I, 497–519).

As is known, about two decades ago coenzyme $B_{12}$ was produced by fermentation from the nutrients of sewage sludge, using the microorganisms present in the sludge. Optionally sewage sludge was supplemented with various further nutrients, too. The process was advantageous in that the fermentation could be carried out under septic conditions, but for each fermentation a large amount of sewage sludge had to be transported to the fermentation plant, the compositions and bacterium population of the sludge were fluctuating, moreover so called "wild strains" could also enter the sewage sludge, by their presence making the formation of a stable micropopulation impossible.

According to a new process disclosed in the Hungarian patent specification No. 153,740 coenzyme $B_{12}$ was produced under anaerobic, aseptic conditions by a process in which to a broth containing the necessary nutrients, sewage sludge was added only once, and after at least five inoculations, a mixed micropopulation was enriched, which could take over the role of inoculum, and produced coenzyme $B_{12}$ in an amount of about 6 to 6.2 mg/lit. of fermentation broth. This so called "sewage sludge-free" process required at least five inoculation steps to adapt the microorganisms of sewage sludge origin to produce coenzyme $B_{12}$, which made the process cumbersome. In addition the coenzyme $B_{12}$ production was low, a large number of different nutrients were required, accordingly, the production costs were rather high.

For the production of coenzyme $B_{12}$ by anaerobic, septic fermentation with aid of a mixed micropopulation, and for the increase of coenzyme $B_{12}$ yield there are numerous further methods known in the art (see e.g. U.S. Pat. Nos. 3,954,971 and 3,979,159), which relate to the intensification of the above "sewage sludge-free" process.

A mesophilic, methane-producing mixed micropopulation was described in the Hungarian patent specification No. 167,658. This mixed micropopulation contained the strains Corynebacterium sp. (24Al), Corynebacterium sp. (62B9), Lactobacillus sp. (244B/Cl) and Propionibacterium sp. (239 Al/b), deposited in the Hungarian National Collection of Medical Bacteria (OKI)

Nation Institute of Hygiene under Nos. 00076, 00077, 00078 and 00079.

This anaerobic, mesophilic, methane-producing mixed micropopulation was, however, difficult to adapt to broths containing unconventional nutrients, six to seven inoculations were necessary. Taking into account that one inoculation cycle takes about seven days, the adaptation of a fermentation based on the above micropopulation for mass production lasts for about 40 to 50 days, which is a very long time and results in high production costs.

The hitherto known processes for the production of coenzyme $B_{12}$ by using anaerobic, mesophilic, methane-producing microorganisms are all characterized in using a large number (about 18 to 20) of different nutrients in a high total concentration. A part of the nutrients is of natural origin such as molasses, beer-yeast hydrolysate, industrial liver extract, cornsteep liquor and sulfite liquor powder, etc. The composition of these nutrients is varying, depending on their origin. Due to this fact, the $B_{12}$ yields are necessarily fluctuating. Other nutrients such as glycine and succinic acid, are expensive.

To eliminate the above disadvantages, the aim of the present invention is
- to reduce the number and specific amount of the nutrients,
- as far as possible to eliminate the natural nutrients, and
- simultaneously keeping the active ingredient production at the same level or increasing same.

We have experimentally found that by using a new inoculum, containing a new, anaerobic, mesophilic, methane-producing micropopulation (as to preparation see Example 1, step a)), and carrying out simultaneously two fermentations: a semicontinuous maintaining and a batchwise producing fermentation,
- the number of nutrients can be reduced to about half of the conventional number,
- the specific amount of nutrients required for most nutrients can be reduced by about 10 to 30%, depending on the specific nutrient,
- the specific material costs of active ingredient production can be reduced by about 20 to 25%,
- of the generally employed five nutrients of natural origin four can be eliminated,
- the expensive glycine and succinic acid can be eliminated,
- cornsteep liquor can be replaced by a heat-treated (hydrolysed) solution thereof (Example 1, Step (a)) or with "corn slops" which is a waste matter formed during the distillery starting from corn starch, or with a hydrolysate thereof (Example 4), while the active ingredient production can be increased by 20 to 30%.

The process according to the invention differs from the known processes in that
- fermentation is carried out with an inoculum containing a new, anaerobic, mesophilic, methane-producing, mixed micropopulation,
- the conversion of the operation of the new batchwise inoculum fermentation suitable for semicontinuous production is completed in 14 to 15 days, unlike in the known processes, in which this step took 40 to 50 days,
- a new broth is employed, in which the number of nutrients is decreased to about half of the conventional number, and their quantity (except methanol and o-xylidine) is reduced by about 10 to 30%, depending on the specific nutrient (see Table 1),
- in place of cornsteep liquor a hydrolysed solution thereof or the so called corn slops (Example 4) or a hydrolysate thereof can advantageously be used.

TABLE

Daily nutrient requirement and active ingredient production, related to the data disclosed in the Hungarian Patent Specification No. 183,549

| Nutrient/active ingredient | Hung. Pat. 183,549 | Example 1 according to the invention |
|---|---|---|
| methanol | 1 | 1.11 |
| cornsteep liquor | 1 | 0.78 |
| ammonium bicarbonate | 1 | 0.78 |
| ammonium sulfate | 1 | 0.92 |
| magnesium chloride | 1 | 0.98 |
| cobalt chloride | 1 | 0.69 |
| 5,6-dimethyl-benzimidazole | 1 | 0.80 |
| o-xylidine | 1 | 1.75 |
| sodium bisulfite | 0 | 1.0 |
| beer-yeast hydrolysate | 1 | 0 |
| industrial liver extract | 1 | 0 |
| molasses | 1 | 0 |
| sulfite lye powder | 1 | 0 |
| ammonium hydroxide | 1 | 0 |
| diammonium hydrogenphosphate | 1 | 0 |
| glycine | 1 | 0 |
| succinic acid | 1 | 0 |
| sodium tripolyphosphate | 1 | 0 |
| acetone | 1 | 0 |
| daily active ingredient production | 1 | 1.3 |

The invention relates to a process for the preparation of a new fermentation broth producing coenzyme $B_{12}$ by means of a new, mesophilic, methane-producing mixed micropopulation, under anaerobic, septic conditions using a new broth containing methanol, precursor(s) and partially known nutrient components, in which the improvement comprises (a) removing 5 to 15 volume percent of the inoculum fermentation broth containing the anaerobic, mesophilic, methane-producing new mixed micropopulation and replacing same with an equal volume of a broth containing cornsteep liquor hydrolysate and/or corn slops or hydrolysate thereof and other known nutrients, the number and concentration of which has been reduced, for 6 to 8 days, and if desired, further manufacturing the fermentation broth removed, (b) after reaching an assimilation velocity of at least 0.15 to 0.2 g methanol/lit. fermentation broth/hour, continuing the removal of fermentation broth as described in step (a) but replacing same with a broth supplemented with ammonium sulfate and o-xylidine, and continuing fermentation for 6 to 8 days, and if desired, further manufacturing the fermentation broth removed, (c) after achieving an assimilation velocity of 0.2 to 0.3 g methanol/lit. fermentation broth/hour—i.e. after converting the inoculum fermentation broth into a maintaining fermentation broth—continuation removal of the fermentation broth and addition of the fresh broth as described in step (b), and if desired, interrupting the removal of fermentation broth for several days, and (d) adding to the removed maintaining fermentation broth on the first day nutrients according to step (b), and if desired, on the second day only methanol, cornsteep liquor or cornsteep liquor hydrolysate and ammonium carbonate and further manufacturing the obtained fermentation broth suitable for batchwise production, and (e) repeating steps (a), (c) and (d) daily.

As described hereinabove, in the process according to the invention 5 to 15 volume percent, preferably 10 volume percent of the inoculum fermentation broth (Example 1, Step (a)) is removed and preferably further manufactured, in spite of its low coenzyme $B_{12}$ concentration, which increases in time. To the remaining inoculum fermentation broth according to a preferred embodiment of the invention broth dissolved in water of 30° to 35° C. or methanol is added. The broth contains the following nutrients:
methanol,
hydrolysed solution of cornsteep liquor,
ammonium bicarbonate,
magnesium chloride,
cobalt chloride,
5,6-dimethyl-benzimidazole and
sodium bisulfite.

In place of cornsteep liquor hydrolysate also cornsteep liquor or corn slops or hydrolysate thereof or mixtures thereof may also be used.

The removal of the 5–15 volume percent, preferably 10 volume percent of the fermentation broth and the addition of an equal volume of broth is continued for 6 to 8 days, while the coenzyme $B_{12}$ production capability of the mixed micropopulation is gradually improved, as can be monitored by the determination of the active ingredient concentration of the fermentation broth and of the velocity of methanol assimilation (furtheron methanolysis). When the velocity of methanolysis becomes 0.2 g of methanol/lit. of fermentation broth/hour, in addition to the previous nutrients
ammonium sulfate and
o-xylidine
are added to the broth, and the semicontinuous fermentation is continued until the velocity of methanolysis becomes 0.3 g of methanol/lit. of fermentation broth/hour (about 7 to 10 days). This corresponds to the equilibrium state of semicontinuous fermentation.

In this manner a semicontinuously operating "maintaining" fermentation broth is obtained, which contains about 15 to 25 mg/lit. of active ingredient. The semicontinuous maintaining fermentation is (may be) continued for at least a year, by removing about 10% of fermentation broth each day and replacing same with an equal volume of a broth as defined above, which is supplemented with ammonium sulfate and o-xylidine.

As soon as the semicontinuous state is achieved, the removed, about 10 volume percent, maintaining fermentation broth is not subjected to further manufacturing any more, instead it is post-fermented for several days (producing fermentation), batchwise.

Batchwise producing fermentation is carried out by adding to the semicontinuous maintaining fermentation broth a fresh broth containing the same nutrients, except magnesium chloride and sodium bisulfite, optionally in different concentrations. If desired, on the second day of batchwise producing fermentation only
methanol,
cornsteep liquor (or an equivalent product as described hereinabove) and
ammonium bicarbonate
are added to the fermentation broth.

The batchwise producing fermentation is completed in two days, and the fermentation broth obtained contains about 26 to 32 mg/lit. of active ingredient, depending on the starting conditions of semicontinuous fermentation and the quality and quantity of nutrients.

The main advantages of the process according to the invention are as follows:
The conversion of the new batchwise inoculum fermentation into a semicontinuous maintaining fermentation takes a short time,
due to an essential reduction in the use of nutrients of natural origin, the active ingredient production of fermentation (semicontinuous maintaining and batchwise producing fermentation) shows practically no fluctuation,
the reduction of the number and quantity of other nutrients improves the economy of the process,
in spite of the use of a broth containing less nutrients in a smaller concentration, the active ingredient concentration produced in a time unit is increased by about 20 to 30%,
due to the reduction of the number of nutrients and primarily due to the omission of nutrients of natural origin, the efficiency of active ingredient production from the fermentation broth is improved.

The process according to the invention is elucidated in detail by the following, non-limiting Examples.

EXAMPLE 1

(a) Preparation of the inoculum

Into a laboratory-scale glass fermenter with 10 lit. working capacity 6000 ml of tap water preheated to 30° to 32° C. are added, followed by the addition of the following nutrients:
35 ml of methanol,
100 ml of a hydrolysate obtained from 50 g of cornsteep liquor,
30 g of ammonium bicarbonate,
1.0 g of magnesium chloride,
0.05 g of cobalt chloride,
0.03 g of 5,6-dimethylbenzylimidazole and
0.30 g of sodium bisulfite.

The culture broth is then thoroughly homogenized and made up to 8000 ml with tap water of 30° to 32° C. To the broth 2000 ml of a postdigested sewage sludge obtained freshly from communal sewage plant are added. The mixture is admixed, the glass fermenter is covered with a rubber plate and placed into a thermostat of 32° to 34° C.

In the following period of fermentation daily 50-ml samples are taken (after homogenization) and 35 ml of methanol are added to the fermenter, whereupon a further 200-ml sample is taken, the fermenter is covered with a rubber plate and anaerobic fermentation is continued for seven additional days, at the same temperature.

The fermentation broth obtained after the first seven days is called 1st generation.

From the sample, taken before the addition of methanol the pH and methanol concentration of the fermentation broth are determined. The 200 ml of fermentation broth removed after the addition of methanol are filled into a gasometer and the velocity of biogas production is determined. The sample is removed from the gasometer and refilled into the fermenter parallel with the addition of the next methanol portion.

On the seventh day of fermentation a 5-times increase of scale is carried out: a fermenter with 50 lit. of working capacity is filled with 30 lit. of tap water of 30° to 32° C., which is then supplemented with the following nutrients
175 ml of methanol, 500 ml of a hydrolysate obtained from 250 g of cornsteep liquor,
150 g of ammonium bicarbonate,
5 g of magnesium chloride,
0.25 g of cobalt chloride,
0.15 g of 5,6-dimethylbenzimidazole,
1.5 g of sodium bisulfite.

When the addition of nutrient is complete, the broth is made up to 40 lit. with tap water of 30° to 32° C.

Thereafter, the total amount (10 lit.) of the seven day's fermentation broth (1st generation) is added to the freshly prepared broth (inoculation) and after intensive homogenization, the fermenter is sealed and anaerobic fermentation is continued at 32° to 34° C. for another seven days.

During the second seven days 50-ml. samples are taken, 175 ml of methanol are added to the fermenter and then 200 ml of samples are taken daily. The fermenter is sealed and fermentation is continued at 32° to 34° C. From the samples removed before and after the addition of methanol, respectively, the pH, methanol concentration and the velocity of biogas production are determined.

The fermentation broth obtained after the second seven days is called the 2nd generation. 10% (5.0 lit.) of the homogenized 2nd generation are removed and an equal volume of a broth having the following composition is added:
5000 ml of tap water of 30° to 32° C.,
175 ml of methanol,
50 ml of a hydrolysate obtained from 25 g of cornsteep liquor,
15 g of ammonium bicarbonate,
0.5 g of magnesium chloride,
0.25 g of cobalt chloride,
0.15 g of 5,6-dimethylbenzimidazole and
0.1 g of sodium bisulfite.

After the addition of the broth, the fermentation broth is thoroughly admixed, the fermenter is sealed and fermentation is continued at 32° to 34° C. for an additional day.

During the above procedure a new, anaerobic, mesophilic, methane-producing mixed micropopulation is formed, containing the strains deposited in the Hungarian National Collection is Medical Bacteria (OKI) Nation Institute of Hygiene under Nos. 00076, 00079 and 00272 [the strains following the order of deposition numbers: Corynebacterium sp. (24 Al), Propionibacterium sp. (239 A₁/6) and Methanococcus sp. (MC-017)]. The inoculum is characterized by a pH of 5.4 to 5.8 and a biogas production of 0.5 to 0.8 lit. of biogas/day/lit. of fermentation broth.

The inoculum obtained is suitable for coenzyme $B_{12}$ production.

The active ingredient concentration of the fermentation broth determined from a sample taken on the first day of semicontinuous operation by the method disclosed in the Hungarian patent specification No. 167,658 amounts to 7.3 mg/lit.

The nutrient components are prepared as follows:
Heat treatment of cornsteep liquor: Cornsteep liquor with an about 45% dry substance content is diluted with an equal volume of tap water, the mixture is brought to the boil and boiled for 15 minutes. The solution is then cooled and made up to the original volume with tap water. The fresh solution obtained is the so called heat-treated cornsteep liquor (hydrolysate).

The suitability of the cornsteep liquor used for the preparation of inoculum for active ingredient production is determined before use by the following microbiological method: Into a laboratory-scale glass fermenter with 10 lit. working capacity 9 lit. of tap water of 30° to 32° C. and subsequently the following nutrients are added:
50 ml of methanol,
50 g of untreated (unhydrolysed) cornsteep liquor containing 45% dry substance, to be tested,
30 g of ammonium bicarbonate,
1 g of magnesium chloride
0.05 g of cobalt chloride,
0.03 g of 5,6-dimethylbenzimidazole and
0.20 g of sodium bisulfite.

After homogenization, 300 ml of fermentation broth from the coenzyme $B_{12}$ fermenter are added to the broth, which is then made up to 10 lit. with tap water of 30° to 32° C. The fermenter is covered with a rubber plate and is placed into a thermostate of 32° to 34° C. Each day 50 ml of methanol are added to the mixture after homogenization, while 200 ml of fermentation broth are removed to determine the velocity of biogas production, the fermenter is covered and fermentation is continued at 32° to 34° C. If on the 4th day of fermentation the biogas production is 0.3 to 0.6 lit./lit. of fermentation broth/day, the cornsteep liquor, after the above-described heat-treatment, is suitable for the preparation of inoculum.

5,6-dimethylimidazole is added to the broth after dissolution in the prescribed amount of methanol.

The other nutrients are directly added to the broth and dissolved therein.

(b) Semicontinuous, maintaining fermentation

About 10% of the inoculum prepared in the fermenter with 50 lit. working capacity is removed daily, and replaced with an equal volume of a maintaining broth, which is prepared as follows:
The following nutrients are dissolved in
5.0 lit. of water of 30° to 35° C.:
300 ml of methanol,
50 ml of a hydrolysed solution of 25 g of cornsteep liquor,
17.5 g of ammonium bicarbonate,
0.5 g of magnesium chloride,
0.05 g of cobalt chloride,
0.03 g of 5,6-dimethyl-benzimidazole, which has previously been dissolved in 10 ml of methanol, and
0.15 g of sodium bisulfite.

After homogenization, the broth is poured into a fermenter with 50 lit. working capacity, containing the fermentation broth. The mixture is thoroughly admixed, the fermenter is sealed and fermentation is performed at 32° to 34° C., under anaerobic conditions.

From the 5-lit. fermentation broth removed daily a sample is taken, and the active ingredient (coenzyme $B_{12}$ and factor III) and methanol content as well as the pH are determined, as described in in Step (a).

On the 6th and 8th day of fermentation, if the velocity of methanolysis becomes 0.2 g of methanol/lit. of fermentation broth/hour,
5 g of ammonium sulfate and
0.2 g of o-xylidine
are also added to the above broth. o-Xylidine is dissolved in 15 ml of methanol.

The removal of 10% of fermentation broth and the addition of the maintaining broth (containing ammonium sulfate and o-xylidine) are repeated daily. In this way the inoculum fermentation is soon transformed into a maintaining fermentation, with an active ingredient content of 17.5 mg/lit.

(c) Batchwise producing fermentation

In order to increase its active ingredient concentration, the 5 lit. of fermentation broth removed daily during the semicontinuous maintaining fermentation is subjected to the following—batchwise—postfermentation:

The fermentation broth is filled into a glass fermenter with 5 lit. working capacity, whereupon the following nutrients are added:
  45 ml of methanol,
  3.5 g of cornsteep liquor (dry substance content: 45%)
  2.5 g of ammonium bicarbonate,
  1.5 g of ammonium sulfate,
  0.005 g of cobalt chloride,
  0.01 g of 5,6-dimethyl-benzimidazole and
  0.01 g of o-xylidine*

*5,6-dimethyl-benzimidazole and o-xylidine are added to the fermentation broth dissolved in 5 ml of methanol, accordingly, the total volume of methanol is 50 ml.

When the addition of nutrients is complete, the fermenter is covered with a rubber plate, and allowed to stand at 32° to 34° C. On the next day (2nd day) the following further nutrients are added:
  20 ml of methanol,
  1.5 g of cornsteep liquor (dry substance content: 45%) and
  1.5 g of ammonium bicarbonate.

When the addition of nutrients is complete, the fermentation broth is again thoroughly admixed, the fermenter is covered with a rubber plate and allowed to stand overnight at 32° to 34° C.

After the second day the active ingredient concentration of the fermentation broth amounts to 26 mg/lit.

EXAMPLE 2

A semicontinuous, maintaining fermentation is carried out as described in Example 1, Step (b). The active ingredient concentration of fermentation broth is 17.5 mg/lit.

The cyclic daily removal of fermentation broth and addition of fresh broth is interrupted for a period of four days in the following manner. On a given day of fermentation only 1 lit. of fermentation broth is removed and on four subsequent days 450 ml of methanol and 250 ml of tap water of 30° to 35° C. containing the following nutrients
  50 g of cornsteep liquor (hydrolysed solution),
  30 g of ammonium bicarbonate,
  10 g of ammonium sulfate,
  0.5 g of magnesium chloride,
  0.15 g of cobalt chloride,
  0.10 g of 5,6-dimethyl-benzimidazole,
  0.10 g of o-xylidine and
  0.10 g of sodium bisulfite
are added, without removing further fermentation broth. From the fifth day on semicontinuous operation is continued in the usual manner, i.e. 5 lit. of fermentation broth are removed daily, and replaced by 500 ml methanol and equal volume of a broth of 30° to 35° C. containing the following nutrients:
  50 g of cornsteep liquor (hydrolysed solution),
  17.5 g of ammonium bicarbonate,
  5 g of ammonium sulfate,
  0.5 g of magnesium chloride,
  0.05 g of cobalt chloride,
  0.03 g of 5,6-dimethyl-benzimidazole,
  0.2 g of o-xylidine and
  0.15 g of sodium bisulfite.

The removal of fermentation broth and the addition of broth are then repeated daily as described above. The active ingredient concentration of the fermentation broth obtained amounts to 24.6 mg/lit.

The 5 lit. of fermentation broth removed daily from the maintaining fermenter are then post-fermented batchwise, in order to increase active ingredient concentration (see Example 1, Step (c)). This step is the batchwise producing fermentation. After post-fermentation for 24 hours the fermentation broth contains 32 mg/lit. of active ingredient.

EXAMPLE 3

This Example illustrates that the use of heat-treated (hydrolysed) cornsteep liquor is more efficient that that of the untreated cornsteep liquor.

Essentially Example 1, Step (b) is followed, but to 5 lit. of broth instead of 50 ml of hydrolysed cornsteep liquor, prepared from 25 g of cornsteep liquor having a dry substance content of 45%, 50 g of untreated cornsteep liquor (dry substance: 45%) are added.

The maintaining fermentation broth will contain 17.0 mg/lit., the fermentation broth obtained after post-fermentation for 48 hours (see Example 1, Step (c)) 25.0 mg/lit. of active ingredient. It can be seen that the active ingredient concentration of both the semicontinuous maintaining and the batchwise producing fermentation broth is practically the same as that of the corresponding fermentation broths prepared in Example 1, Steps (b) and (c), in spite of the double amount of cornsteep liquor employed in the present Example.

EXAMPLE 4

Essentially the procedure described in Example 1, Step (b) is followed, except that into the daily broth of the 50-lit. semicontinuous production fermenter instead of the 50 ml of hydrolysed cornsteep liquor solution (prepared from 25 g of cornsteep liquor) 150 ml of a solution prepared by the hydrolysis of 75 g of corn slops (dry substance content: 30%) are added. The heat-treatment (hydrolysis) of corn slops is carried out as described in connection with the hydrolysis of cornsteep liquor (Example 1).

During post-fermentation according to Example 1, Step (c) the 3.5 g and 1.5 g of cornsteep liquor added in the first and second day, respectively and containing 45% of dry substance, are replaced by 5.25 g and 2.25 g of heat-treated corn slops. The active ingredient concentration of the fermentation broth obtained after post-fermentation for two days amount to 25.2 mg/lit.

As illustrated by the present Example, cornsteep liquor and hydrolysate thereof can be replaced by heat-treated corn slops.

We claim:

1. A process for the preparation of a fermentation broth containing Coenzyme $B_{12}$ which comprises the following steps:
   (a) providing an inoculum fermentation broth containing anaerobic, mesophilic methane-producing bacteria of a mixed population, said mixed population comprising strains deposited in the Hungarian National Collection, National Institute of Hygiene, Nos. 00076, 00079, and 00272;

(b) removing 5 to 15 vol % of the inoculum fermentation broth containing the anaerobic, mesophilic methane-producing mixed bacteria, and replacing same with an equal amount of a first mutrient broth, and after homogenization, anaerobically fermenting the inculum fermentation broth at 32° to 34° C. for 6 to 8 days;

(c) after reaching an assimilation velocity of at least 0.15 to 0.2 g methanol/liter fermentation broth/hour, continuing the removal of fermentation broth as described in step (b) but replacing the fermentation broth removed with a maintaining broth supplemented with ammonium sulfate and o-xylidene, and continuing fermentation for about 7 to 10 days, until the velocity of methanolysis reaches 0.3 g of methanol/liter of fermentation broth/hour, thereby reaching a state of semi-continuous fermentation;

(d) obtaining a semicontinuously operating maintaining fermentation broth which contains about 15 to 25 mg/liter of Coenzyme $B_{12}$;

(e) determining the content of the methanol and Coenzyme $B_{12}$ of the inoculum fermentation broth removed during step (b) as well as the pH thereof;

(f) treating the inoculum fermentation broth removed during step (b) with additional nutrients to obtain a second fermentation broth having about 26 to 32 mg/liter of Coenzyme $B_{12}$; and (g) repeating steps (b), (d), (e) and (f) daily.

2. The process as defined in claim 1, wherein in steps (a) and (b), instead of a hydrolysate of corn steep liquor, a mixture of a hydrolyzed solution of corn steep liquor and corn slop is employed.

3. The process as defined in claim 1, wherein in steps (a) and (b), instead of a hydrolysate of corn steep liquor, heat-treated corn slops is employed.

4. The process as defined in claim 1, wherein in steps (d) the concentration of Coenzyme $B_{12}$ is 17.5 mg/liter.

5. The process as defined in claim 1, wherein in step (f) the concentration of Coenzyme $B_{12}$ is 26 mg/liter.

6. The process defined in claim 1 wherein said first broth consists essentially of:
   175 ml of methanol;
   500 ml of a hydrolysate obtained from 150 g of corn steep liquor;
   150 g of ammonium bicarbonate;
   5 g of magnesium chloride;
   0.25 g of cobalt chloride;
   0.15 g of 5,6-dimethyl-benzimidazole; and
   1.5 g of sodium bisulfide per 30 liters of tap water;

and said additives per 5 liters in step (b) consisting essentially of:
   45 ml of methanol;
   3.5 g of cornsteep liquor having a dry substance content of 45%;
   2.5 g of ammonium bicarbonate;
   1.5 g of ammonium sulfate;
   0.05 g of cobalt chloride;
   0.01 g of 5,6-dimethyl-benzimidazole; and
   0.01 g of o-xylidene.

* * * * *